United States Patent [19]
Ezekowitz

[11] Patent Number: 5,270,199
[45] Date of Patent: Dec. 14, 1993

[54] HUMAN MANNOSE-BINDING PROTEIN

[75] Inventor: Raymond A. B. Ezekowitz, Boston, Mass.

[73] Assignee: The Children's Medical Center Corporation, Boston, Mass.

[21] Appl. No.: 831,619

[22] Filed: Feb. 6, 1992

Related U.S. Application Data

[63] Continuation of Ser. No. 417,822, Oct. 5, 1989, which is a continuation-in-part of Ser. No. 87,628, Aug. 20, 1987, abandoned.

[51] Int. Cl.$^5$ .............. C12N 5/00; C12N 15/00; C12N 7/00; C12N 1/21; C12N 1/16; C12N 1/18; C12P 21/02; C12P 19/34; C02K 3/00; C07H 15/12

[52] U.S. Cl. .................. 435/240.2; 435/69.1; 435/172.3; 435/320.1; 435/235.1; 435/252.3; 435/252.33; 435/254.11; 435/254.2; 536/23.4; 536/23.5; 530/350; 935/18; 935/27; 935/32; 935/34; 935/38; 935/55; 935/62; 935/70; 935/72

[58] Field of Search ............ 435/69.1, 91, 172.3, 435/235.1, 320.1, 240.2, 252.3, 252.33, 255, 256; 536/27; 530/350; 535/18, 27, 32, 34, 38, 55, 62, 70, 72

[56] References Cited

U.S. PATENT DOCUMENTS 4,675,382 6/1987 Murphy .................. 530/350

FOREIGN PATENT DOCUMENTS 8303971 5/1983 World Int. Prop. O.

OTHER PUBLICATIONS

Sieggs et al. Proc. Natl. Acad. Sci. U.S.A. vol. 78 pp. 6613–6617 (1981).
Maniahs et al. Molecular Cloning A Laboratory Manual Cold Spray Harbor Laboratory, CSH, N.Y. (1982) pp. 404–423.
Taylor et al., "Mammalian Mannose-Binding Proteins", Clinical Science, 70: 539–546 1986.
Summerfield et al., "Mannose-Binding Proteins in Human Serum: Identification of Mannose-Specific Immunoglobulins and a Calcium-Dependent Lectin, of Broader Carbohydrate Specificity, Secreted by Hepatocytes", Biochimica et Biophysica Acta, 883: 197–206 1986.
Stahl et al., "Mannose-Specific Oligosaccharide Recognition by Mononuclear Phagocytes", Biol. Cell, 51: 215–218 1984.
Wild et al., "Isolation of Mannose-Binding Proteins from Human and Rat Liver", Biochem. J., 210: 167–174 1983.
Drickamer et al., "Mannose-Binding Proteins Isolated from Rat Liver Contain Carbohydrate-Recognition Domains Linked to Collagenous Tails", J. of Bio. Chemistry, 261: 6878–6887 1986.
Ikuta et al., "Human Lymphocyte Fc Receptor for IgE: Sequence Homology of Its Cloned cDNA with Animal Lectins", Proc. Natl. Acad. Sci. U.S.A., 84: 819–823 1987.
Drickamer, "Two Distinct Classes of Carbohydrate-Recognition Domains in Animal Lectins", J. of Bio. Chemistry, 263: 9557–9560 1988.
Drickamer et al., "Exon Structure of a Mannose-Binding Protein Gene Reflects Its Evolutionary Relationship to the Asialoglycoprotein Receptor and Nonfibrillar Collagens", J. of Bio. Chemistry, 262: 2582–2589 1987.
Haagsman et al., "The Major Lung Surfactant Protein, SP 28–36, Is a Calcium-Dependent, Carbohydrate-Binding Protein", J. of Bio Chemistry, 262: 13877–13880 1987.
White et al., "Isolation and Characterization of the Human Pulmonary Surfactant Apoprotein Gene", Nature, 317: 361–363 1985.

(List continued on next page.)

*Primary Examiner*—Joan Ellis
*Attorney, Agent, or Firm*—Fish & Richardson

[57] ABSTRACT

Purified human mannose-binding protein and fragments thereof, nucleic acid producing these fragments, and vectors and cells including such nucleic acid are disclosed. The peptides and antibodies to those peptides are useful for diagnosis and treatment of disease.

13 Claims, 6 Drawing Sheets

OTHER PUBLICATIONS

Valenzuela et al., "Synthesis and Assembly of Hepatitis B Virus Surface Antigen Particles in Yeast", Nature, 298: 347-350 1982.

Mackett et al., "Vaccinia Virus: A Selectable Eukaryotic Cloning and Expression Vector", Proc. Natl. Acad. Sci. U.S.A., 79: 7415-7419 1982.

Ezekowitz et al., "Abstract", Clinical Research, 35: p. 607A (1987).

Ezekowitz et al., "A Human Mannose-Binding Protein is an Acute-Phase Reactant That Shares Sequence Homology With Other Vertebrate Lectins", J. Exp. Med., 167: 1034-1046 1988.

Kuhlman et al., "The Human Mannose-Binding Protein Functions as an Opsonin", J. of Exp. Med., 169: 1733-1745.

Horwitz, "The Role of Human Mannose-Lectin-like Molecules in Host Defense", Bacteria-Host Cell Interaction, pp. 213-223 1988.

```
  1 GGTAAATATGTGTTCATTAACTGAGATTAACCTTCCCTGAGTTTTCTCACACCAAGGTGA  60
 61 GGACCATGTCCCTGTTTCCATCACTCCCTCTCCTTCTCCTGAGTATGGTGGCAGCGTCTT 120
        MetSerLeuPheProSerLeuProLeuLeuLeuLeuSerMetValAlaAlaSerT
121 ACTCAGAAACTGTGACCTGTGAGGATGCCCAAAAGACCTGCCCTGCAGTGATTGCCTGTA 180
    yrSerGluThrValThrCysGluAspAlaGlnLysThrCysProAlaValIleAlaCysS
181 GCTCTCCAGGCATCAACGGCTTCCCAGGCAAAGATGGGCGTGATGGCACCAAGGGAGAAA 240
    erSerProGlyIleAsnGlyPheProGlyLysAspGlyArgAspGlyThrLysGlyGluL
241 AGGGGGAACCAGGCCAAGGGCTCAGAGGCTTACAGGGCCCCCCTGGAAACTTGGCCCCTC 300
    ysGlyGluProGlyGlnGlyLeuArgGlyLeuGlnGlyProProGlyLysLeuGlyProP
301 CAGGAAATCCAGGGCCTTCTGGGTCACCAGGACCAAAGGGCCAAAAAGGAGACCCTGGAA 360
    roGlyAsnProGlyProSerGlySerProGlyProLysGlyGlnLysGlyAspProGlyL
361 AAAGTCCGGATGGTGATAGTAGCCTGGCTGCCTCAGAAAGAAAAGCTCTGCAAACAGAAA 420
    ysSerProAspGlyAspSerSerLeuAlaAlaSerGluArgLysAlaLeuGlnThrGluM
421 TGGCACGTATCAAAAAGTGGCTGACCTTCTCTCTGGGCAAACAAGTTGGGAACAAGTTCT 480
    etAlaArgIleLysLysTrpLeuThrPheSerLeuGlyLysGlnValGlyAsnLysPheP
481 TCCTGACCAATGGTGAAATAATGACCTTTGAAAAAGTGAAGGCCTTGTGTGTCAAGTTCC 540
    heLeuThrAsnGlyGluIleMetThrPheGluLysValLysAlaLeuCysValLysPheG
541 AGGCCTCTGTGGCCACCCCCAGGAATGCTGCAGAGAATGGAGCCATTCAGAATCTCATCA 600
    lnAlaSerValAlaThrProArgAsnAlaAlaGluAsnGlyAlaIleGlnAsnLeuIleL
601 AGGAGGAAGCCTTCCTGGGCATCACTGATGAGAAGACAGAAGGGCAGTTTGTGGATCTGA 660
    ysGluGluAlaPheLeuGlyIleThrAspGluLysThrGluGlyGlnPheValAsnLeuT
661 CAGGAAATAGACTGACCTACACAAACTGGAACGAGGGTGAACCCAACAATGCTGGTTCTG 270
    hrGlyAsnArgLeuThrTyrThrAsnTrpAsnGluGlyGluProAsnAsnAlaGlySerA
721 ATGAAGATTGTGTATTGCTACTGAAAAATGGCCAGTGGAATGACGTCCCCTGCTCCACCT 780
    spGluAspCysValLeuLeuLeuLysAsnGlyGlnTrpAsnAspValProCysSerThrS
781 CCCATCTGGCCGTCTGTGAGTTCCCTATCTGAAGGGTCATATCACTCAGGCCCTCCTTGT 840
    erHisLeuAlaValCysGluPheProIle
841 CTTTTTACTGCAACCCACAGGCCCACAGTATGCTTGAAAAGATAAATTATATCAATTTCC 900
901 TCATATCCAGTATTGTTCCTTTTGTGGGACAATCACTAAAAATGATCACTAACAGCACCA 960
961 ACAAAGCAATAATAGTAGTAGTAGTAGTTAGCAGCAGCAGTAGTAGTCATGCTAATTATA 1020
1021 TAATATTTTAATATATACTATGAGGCCCTATCTTTTGCATCCTACATTAATTATCTAGT 1080
1081 TTAATTAATCTGTAATGCTTTCGATAGTGTTAACTTGCTGCATGAAAATAAGACGGA 1140
1141 TTTATTTTTCCATTTACAACAAACACCTGTGCTCTGTTGAGCCTTCCTTTCTGTTTGGGT 1200
1201 AGAGGGCTCCCCTAATGACATCACCACAGTTTAATACCACAGCTTTTTACCAAGTTTCAG 1260
1261 GTATTAAGAAAATCTATTTTGTAACTTTCTCTATGAACTCTGTTTTCTTTCTAATGAGAT 1320
1321 ATTAAACCATGTAAAGAACATAAATAACAAATCTCAAGCAAACAGCTTCACAAATTCTCA 1380
1381 CACACATACATACCTATATACTCACTTTCTAGATTAAGATATGGGACATTTTTGACTCCC 1440
1441 TAGAAGCCCCGTTATAACTCCTCCTAGTACTAACTCCTAGGAAAATACTATTCTGACCTC 1500
```

FIG. 2A

```
1501 CATGACTGCACAGTAATTTCGTCTGTTTATAAACATTGTATAGTTGGAATCATATTGTGT 1560
1561 GTAATGTTGTATGTCTTGCTTACTCAGAATTAAGTCTGTGAGATTCATTCATGTCATGTG 1620
1621 TACAAAAGTTTCATCCTTTTCATTGCCATGTAGGGTTCCCTTATATTAATATTCCTCAGT 1680
1681 TCATCCATTCTATTGTTAATAGGCACTTAAGTGGCTTCCAATTTTTGGCCATGAGGAAGA 1740
1741 GAACCCACGAACATTCCTGGACTTGTCTTTTGGTGGACATGGTGCACTAATTTCACTACC 1800
1801 TATCCAGGAGTGGAACTGGTACAGGATGAGGAAAGCATGTATTCAGCTTTAGTAGATTAT 1860
1861 ACCAGTTTTCCTAACTCATTGTATGAATTTATGCTCCTACGCAATGTGTGGCAGTCCTAG 1920
1921 ATGCTCTATGTGCTTGTAAAAGTCAATGTTTCATTTATCCTGTGGATGTAAAGTGATATT 1980
1981 TGCCCATGGTTTTAATCTGTATTTTCCCAACATGTAATAAGGTTGAACACTTTTTTATAT 2040
2041 GCTTATTGGGCACTTGGGTATCTTCTTCTGTGAAGTACCCGTTCACATTTTGTATTTTG 2100
2101 TTTAAATTAGTTAGCCAATATTTTTCTTACTGATTTTTAAGTTATTTTTACATTCTGAAT 2160
2161 ATGTCCTTTTTAATGTGTATTACAAATATTTTGCTAGTTTTTGACTTGCTCCTAATGTTG 2220
2221 AATTTTGATGAACAAAATTTCCTAATTTTGAGAAAGTCTTATTTATTCATATTTTCTTTC 2280
2281 AAAATTAGTGCTTTTTGTGCATGTTTAAGAAATTTTTGCCCATCCCAAAATCATAAGATA 2340
2341 TTTTTCATGATTTTGAAACCATGAAGAGATTTTTCATGATTTTGAAATCATGAAGATATT 2400
2401 TTTCCATTTTTTTCTAATAGTTTTATTAATAAACATTCTATCTATTCCTGGTAGAATAGA 2460
2461 TATCCTCTTGAGACAGCACTATGTAGGAAAGACCATTTTTGCAGCCACCTGAACTAGGGT 2520
2521 GGTGCATTTTTGTAAGTTAGGTAACTGTATGTGTGTGTCTGTTTCTGGGCTGTCTATT 2580
2581 CTAGTCTATTTGTTGATGCTTGTGTCAAACAGTCAACACTATCTTAATTATTGTACAATTAT 2640
2641 AGTTGTAACTGTAGTCCAGCTTTGTTCTTCTTCAAGTCAAGATTTCCATATAAATATTAG 2700
2701 AAACAGTTTCTCAATTTCTACAAAATCTGATGAGGTTTCTACTGGGACCACATTGAGTCT 2760
2761 ATCAATCAACTTATGCAGAACTGGCAACTTACTACTGATCTCTAATCAATGTTCATCATG 2820
2821 TATCGCTTCATTTAACTAGGATTTCTCTAACTTAATTGCTATGTTTTGAGATTTTTAGTT 2880
2881 TAAAAACCTTGTATATCCTGTTTTGGTGGTTTTAGTGATTTTAATAATATATTTTAATA 2940
2941 TTTTTTCTTTTCTATTGTTGTACACAGAAATACAGTTAAGTTTTGTGTGTAGTCTTACGA 3000
3001 TGTTTAGTAACCTCAATAAGTTTATTTCTTAAATCTAGTAATTTGTAGATTCCTCTGGAT 3060
3061 TTTGTATATGCATAGTCATGTAAGCTGAAAATATGGCAATACTTGCTTCTCCCCAATTGC 3120
3121 TTTACCTTTTTTCTTACCTTATTGCACTGGTTAGCAACCCCAATACAGAGACCACCAGAG 3180
3181 CAGGTATAGACTCCTGAAAGACAATATAATGAAGTGCTCCAGTCAGGCCTATCTAAACTG 3240
3241 GATTCACAGCTCTGTCACTTAATTGCTACATGATCTAGGAGCCAGTTACTTTGTGTTTCA 3300
3301 GCCATGATTTGCAGCTGAGAGAAAATAATCATTCTTATTTCATGAAAATTGTGGGGATTG 3360
3361 ATGAAATAAGTTAACXCCTTTAAAGTGTGTAGTAAAGTATCAGGATACTATATTTTAGGT 3420
3421 CTTAATACACACAGTTATGCCGCTAGATACATGCTTTTTAATGAGATAATGTGATATTAT 3480
3481 ACATAACACATATCGATTTTTAAAAATTAAATCAACCTTGCTTTGATGGAATAAACTCCA 3540
3541 TTTAGTCACAAAAAAAAAAAAAAAAAAAAAAAAAAAAAAAAAAAAAAGAATTC 3592
```

FIG. 2B

```
gaattcctgccagaaagtagagaggtatttagcactctgccagggccaacgtagtaagaaattccagagagaaatgcttaccaggcaagcctgtgtaaaacaccaaggggaagcaaact
ccagtaattctgggctggtgactaaggttgagtttgactaaggttgagcctttgatcaccagctttcagctcaggcctgcaatgagtaatgatagttaacag
gtcctggaggggaatcagctgccagatacaaagatgggattcaggtggcagaagatggacccgaagaggagaaatgcctacagacaccctggtttccactcattctc
attccctaagctaacaggcagcataagctggcaatgcagtcggtcccattttgttctcagcagcaacgccagttgctcagcacagatgaa
cccctcttagatctctatagcctgcacccagattgtaggacagaggcatgctcGGTAAATATGTGTTCATTAACTGAGATTAACCTTTCTCAGTTTTCACACCAAGGTGAGGACCATGTCC
tctattctatatagcctgcacccagattgtaggacagaggcatgctcGGTAAATATGTGTTCATTAACTGAGATTAACCTTTCTCAGTTTTCACACCAAGGTGAGGACCATGTCC
                                                                                                   MetSer
CTGTTTCATCACTCCCTCCTTCTCCTGAGATGTGGTGGCAGCGTCTTACTCAGAAACTGTGACCTGTGAGGATGCCAAAGACTGCCTGCAGTGATTGCCTGTAGCTCTCCAGGC
LeuPheProSerLeuProLeuLeuLeuSerMetValAlaAlaSerTyrSerGluThrValThrCysSerGluAspAlaGlnLysThrCysProAlaValIleAlaCysSerSerProGly
ATCAACGGCTTCCAGGCAGAAAGATGGGCGTGATGCCGTGAACCAGgtacgtgtttgggctgttctgctgcaattccctgaggaaactgccctggg
IleAsnGlyPheProGlyLysThrLysGlyGluLysLysT
gatatgagagactgatgtcctatttgagtatattttctcaactataccagtgtaactcaaaacagagattcagctgactcaaaacagagattcagctgactgactaatagtgtcttgtcttgactaatagtgtcttgcc
aggaaagtgcccacagtcagcagcaacaaacataggtttactggggacacagaggatgaattttttctcattgtcatcattgtcagaccctccgtggtcatttcatgtcagaccctccgtg
caaagagagatggagtcagcagcaacaaacataggtttactggggatcttgttctactggggatcttgttgtggacagttgctctcagtgtgacaccatacagttattgagagcagtgctcagaaaggtcagtc
taattttcactttgcacctctcccctgagaaagggattgggcatcaaactcttgaagagagagcaagaacatagatatttaagtcacattccttgtcttccaacagCCAAGGCTCAGAG
                                                                                                   lyGlnGlyLeuArgG
tgggtcaagtctcccctctcccctgagaaagggattgggcatcaaactcttgaagagagagcaagaacatagatatttaagtcacattccttgtcttccaacagCCAAGGCTCAGAG
GCTTACAGGGCCCCCCCTGGAAAGTTGGGCCTCTGGGCCCCTGGGCCCTGGGCCCTGGGTCACCAGGAAATCCAGGGCCCTTCAGGGCCTTCACCAGGACCAAAAGGAGACCCTGGAAAAGTCCGgtaaggaccccagcaagg
lyLeuGlnGlyLeuProProGlyLysLeuGlyLeuProProGlyLysLeuGlyLeuGlyProProGlyLysProGlyLeuProProGlyLysProGlyAsnProGlySerGlySerProGlyLysProGlyLysProGlyAspProGlyLysSerProA
tctgagctgacttcaccagggttctgagacctttgagtatctggtaagagggtgcccccttcaagggagatacccaaattgcttttgacccagctgccctgccc
tc....cagtttgaaaaagatactccactccttgtatatgcacagttctgaggctcttcttcttcaacaatgtcttcttgttcttaattttgttctagATGGTGATAGTAGGCCTGCC
                                                                                                   SPGlyAspSerSerLeuAlaAla
TCAGAAGAAAAGCTCTGCAAACAGAAATGGCACGTATCAAAAGTgtaagcttttctcttttctcttttctcttcttccaggcagcttgaagttttgggaaaatagaatgcaacaaatatttgtttgaatg
SerGluArgGlyLysAlaLeuGlnThrGluMetAlaArgIleLysLysT
catataatttctgta.......tatatgggagatatactaaaatattcattgatggacatggacatggacatggatctgaattcaaattaactgatgactgctgaagactctcatatttggcacctactctagaagact
ttttcttgagaaatacctgagttgggcttaaggactgggagtatgatgagtctgaaattttcacattttcacacctactttgaaactttaGGGCTGACCTTCTCTGGGCAAACAAGTTGGAACAAGTTCTTCCTGACCAA
                                                                                                   rpLeuThrPheSerLeuGlyLysGlnValGlyLysAsnLysPhePheLeuThrAs
```

HUMAN MANNOSE-BINDING PROTEIN

BACKGROUND OF THE INVENTION

This is a continuation of application Ser. No. 07/417,822, filed Oct. 5, 1989, now abandoned, which application is a continuation-in-part of Ezekowtiz, U.S. patent application Ser. No. 087,628, entitled "Human Mannose-Binding Protein" filed Aug. 20, 1987, now abandoned, the whole of which is hereby incorporated by reference herein.

This invention relates to proteins able to bind mannose.

Mannose-binding proteins (MBPs) have been isolated from rabbit, rat, and human liver. Taylor et al. *Clinical Science* 70:539, 1986. MBPs have also been found in serum, and may play a role in the disposal of pathogenic organisms. Id.

Summerfield et al. *Bioc. Biop. Acta* 883:197, 1986 describe two types of MBPs in human serum. These were detected using antibodies raised against a 30 kDa subunit of one MBP. The authors suggest that MBPs may bind noxious glycoproteins in the circulation prior to the removal of these glycoproteins; and that yeasts and bacteria contain glycoproteins which are bound by MBPs.

Stahl et al. *Biol. Cell* 51:215, 1984 describe a mannose receptor, which is distinct from MBP. These two proteins appear to be structurally related since antibodies to one protein may react with the other protein.

Wild et al. *Biochem. J.* 210:167, 1983 describe the isolation of MBP from human and rat liver. The human MBP has a molecular weight greater than one million and consists of 28 kDa and 30.5 kDa subunits.

Drickamer et al. *J. Biol. Chem.* 261:6878, 1986 describe the isolation of MBPs from rat liver, and the cloning of cDNAs encoding these proteins. Each MBP has a cysteine rich region, a collagen like domain and a carbohydrate binding domain.

SUMMARY OF THE INVENTION

In one aspect, the invention features engineered nucleic acid encoding for at least 20, preferably 60, 150, or even more preferably 350, contiguous amino acids of a portion of human mannose-binding protein, useful for targeting cells expressing mannose, N-acetylglucosamine, or fucose, useful for fixing complement, or useful as an antigen for formation of antibodies to human mannose binding protein.

By "engineered nucleic acid" is meant nucleic acid removed from its natural environment (i.e., from naturally adjacent nucleic acid) by recombinant DNA methodology, or synthetic nucleic acid, or cDNA. This nucleic acid may be a fragment of DNA or RNA, it may be present in a vector system (e.g., a plasmid, cosmid or phage), or it may be within the genome of an organism. Such nucleic acid is also referred to as purified nucleic acid, and includes a homogeneous preparation of desired nucleic acid. By "useful for targeting cells" is meant that the portion of human mannose-binding protein can specifically recognize pathogenic cells (e.g., bacteria, fungi, or viruses) having exposed configurations of the specified sugar moieties on their cell wall or envelope glycoprotein, and thus be used as a probe for those cells, or as a tool for delivery of specific molecules (e.g., toxins or cell specific molecules such as the T-cell antigen, CD4) to those cells, or as an in vivo marker for those cells to the immune system. By "useful for fixing complement" is meant that the portion is able to bind to the serum proteins collectively called complement, and thereby stimulate the binding of macrophages to the protein and subsequent ingestion by those macrophages. By "useful as an antigen" is meant that the portion is active to provoke an immune response to cause production of antibodies to a human mannose-binding protein.

In preferred embodiments, the nucleic acid is cDNA and encodes a peptide having greater than 75% homology to a fragment of at least 60, preferably 150, or even more preferably 350, contiguous amino acids of human mannose binding protein; most preferably the nucleic acid encodes for human mannose-binding protein. In other preferred embodiments, the nucleic acid encodes the carbohydrate binding region, the amino-terminal region, the collagen-like region (which includes the complement-fixing portion), or the cell-binding domain of human mannose binding protein; most preferably, the nucleic acid includes at least, or has 75% homology with, the 150 bases, from region 366-813 shown in FIG. 2; and the nucleic acid is ligated to nucleic acid encoding the toxic part of a toxin molecule (e.g., AZT, ricin, or cholera toxin), to nucleic acid encoding a peptide useful for fixing complement, or useful as an antigen for formation of antibodies to human mannose-binding protein. Even more preferably, the nucleic acid is ligated to nucleic acid encoding a molecule useful for targeting a virus, e.g., the molecule is the T cell antigen CD4 and the virus is that causative of an autoimmune disease, such as HIV-1. The hybrid peptides encoded by such ligated nucleic acid are especially useful for causing a toxic type molecule to be targeted to an undesired cell or other organism, such as a virus. Other useful hybrid peptides include those encoded by nucleic acid encoding the complement-fixing portion of human mannose-binding protein ligated to nucleic acid encoding a molecule, such as CD4 useful for targeting a virus.

In a related aspect, the invention features a fragment of at least 150 contiguous bases of the nucleic acid encoding human mannose-binding protein deposited in the ATCC as strain number ATCC 67483 and chosen from nucleic acid encoding for a peptide useful for targeting cells expressing mannose, N-acetylglucosamine, or fucose, a peptide useful for fixing complement, or a peptide useful as an antigen for formation of antibodies to human mannose-binding protein. Most preferably, the nucleic acid substantially corresponds to the nucleic acid encoding human mannose-binding protein deposited in the ATCC as strain number ATCC 67483.

In other aspects, the invention features recombinant human mannose-binding protein, an expression vector, or a cell containing the vector, each vector having the engineered nucleic acid described above, and purified recombinant peptides expressed from these vectors or cells. In preferred embodiments, the cell is a virus (e.g., vaccinia), bacterium (e.g., *Escherichia coli*), fungus (e.g., yeast), or eucaryotic cell (e.g., a cultured cell line). By peptide is meant a chain of about ten or more amino acids, including proteins and polypeptides which are useful in this invention as discussed above. By recombinant peptide is meant a peptide, as described above, or a portion of human mannose-binding protein, that is expressed from engineered nucleic acid.

The peptides described above, and antibodies to those peptides, may be used as therapeutic or diagnostic agents. Preferably the peptide is purified, that is, the peptide is substantially separated from contaminating peptides, most preferably it is provided as an homogenous preparation admixed in a carrier substance suitable for therapeutic use. By therapeutic agent is meant a substance useful for the treatment of a disease or disorder; by diagnostic agent is meant a substance relating to the detection of a disease or disorder.

In yet other aspects, the invention features methods for treating an animal, e.g., a human, infected with a bacterium, fungus, or virus. One such method includes providing and administering a therapeutically effective amount of a therapeutic agent or peptide including a portion of human mannose binding protein inhibitory to the growth of, or infection by, the bacterium, fungus or virus, or a therapeutic peptide useful for targeting cells expressing mannose, N-acetylglucosamine, or fucose or for fixing complement. The therapeutic agent or peptide causes direct inhibition of growth of the infective organism, or causes host defensive cells, e.g., macrophages, to be attracted to the pathogenic organisms which are thereby inactivated. Such inactivation may be aided by the presence of complement which is fixed by the peptide. A therapeutically effective amount is that quantity which produces a significant physiological effect in the patient, and is recognized by those of ordinary skill in the art to depend upon the size and weight of the animal as well as other well known factors.

In preferred embodiments, the peptide is a therapeutically effective fragment of human mannose-binding protein; the peptide is able to inhibit (e.g. reduce or prevent) growth of, or infection by, the bacterium, fungus, or virus, and is a peptide as described above. Most preferably, the animal is human; the infection is one that results in a bacteremia or local bacterial infection, parasitic infection, or fungal colonization, and the route of administration is either intravenous, intramuscular, oral, or local, e.g., in the form of a powder, or lotion, preferably at 5-100 µg/ml, more preferably at 25 µg/ml; or the virus is HIV or a related virus, and the peptide lowers the rate of infection of eucaryotic cells by the virus; the protein or peptide is a portion of mannose-binding protein provided at 1-500 µg/ml (preferably 150 µg/ml) final concentration in human serum or tissue. Alternatively, lipid vesicles, or lyposomes, containing toxins or antibiotics are coated with the peptide and administered directly to the patient. Such lyposomes will be targeted to the infected area by the peptide and the content of the lyposomes released, thereby specifically retarding or preventing growth of the targeted cells or organisms in the targeted area.

In a related aspect, the invention features a coated catheter, useful for long-term administration of fluids to a patient. The catheter is coated with one of the above-described peptides, e.g., by impregnating the catheter material with the peptide. The peptide lowers the rate of bacterial, fungal or viral infection of the patient through the catheter.

In other aspects, the invention features methods for diagnosing infection by a bacterium, fungus or virus, for diagnosing a patient's susceptible to such infection, and for predicting imminent infection of a patient. The methods include detecting the serum level of a mannose-binding protein in a patient. This level reflects the infection of the patient, the susceptibility of the patient to an infection, or the imminence of infection.

Preferably, the methods feature detecting reaction of an antibody to one of the above peptides with the serum of a patient; most preferably the detecting is by an enzyme linked immunosorbent assay (ELISA) test.

In a final and related aspect, the invention features a purified antibody useful for detecting the presence of an above described recombinant peptide, or a human mannose binding protein. The antibody is preferably provided as a homogeneous preparation of a monoclonal or polyclonal antibody. The antibody is useful for purification of human mannose-binding proteins or peptides thereof, for therapeutic treatment of patients, and for diagnosis of infection, of susceptiblity to infection, or of imminence of infection, as disclosed above.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIGS. 2A and 2B show the nucleotide base sequence and corresponding amino acid sequence of human mannose-binding protein cDNA. Appropriate portions of exons are shown.

Figure 4B:
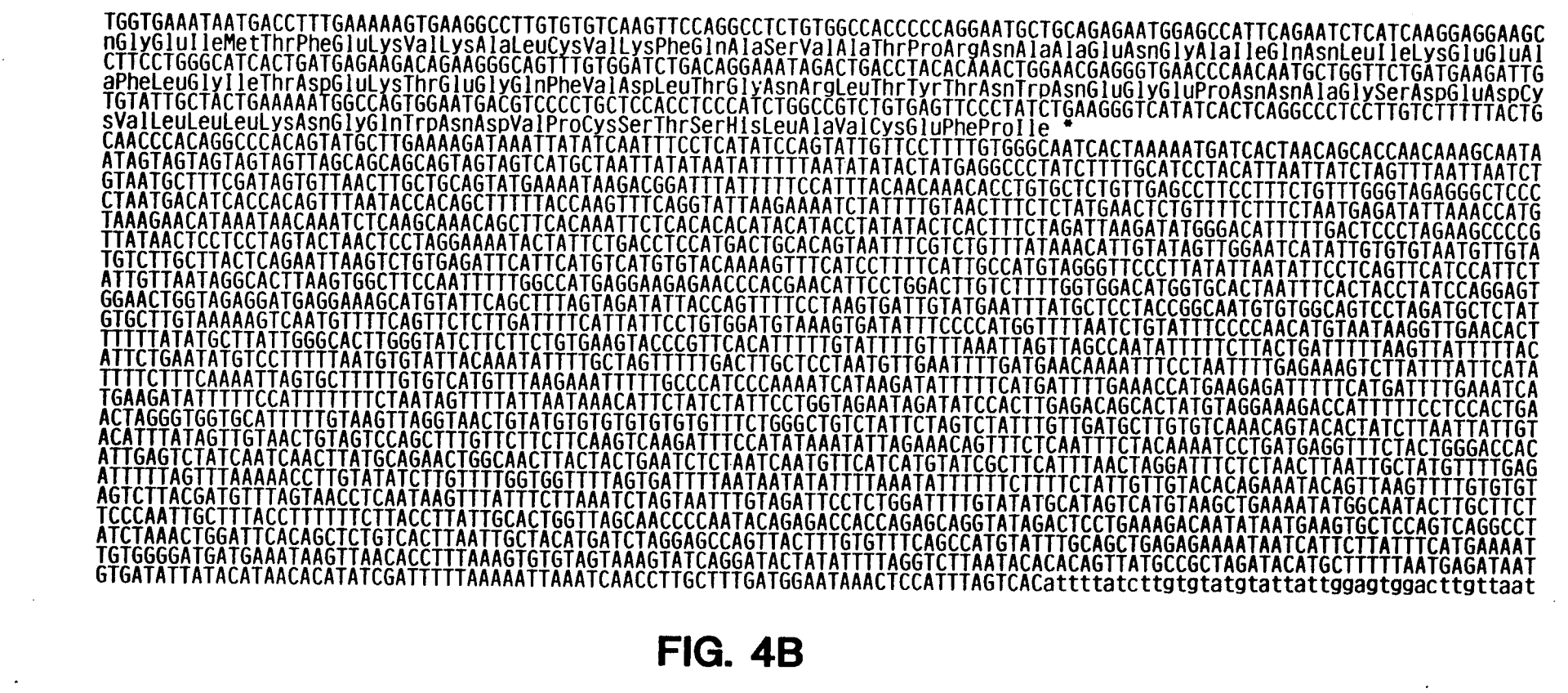

FIGS. 4A and 4B show the nucleotide base sequence and corresponding amino acid sequence of the human mannose binding protein genomic DNA. The asterix designated a translational stop codon. Bases shown in small letters are parts of introns.

Figure 5:
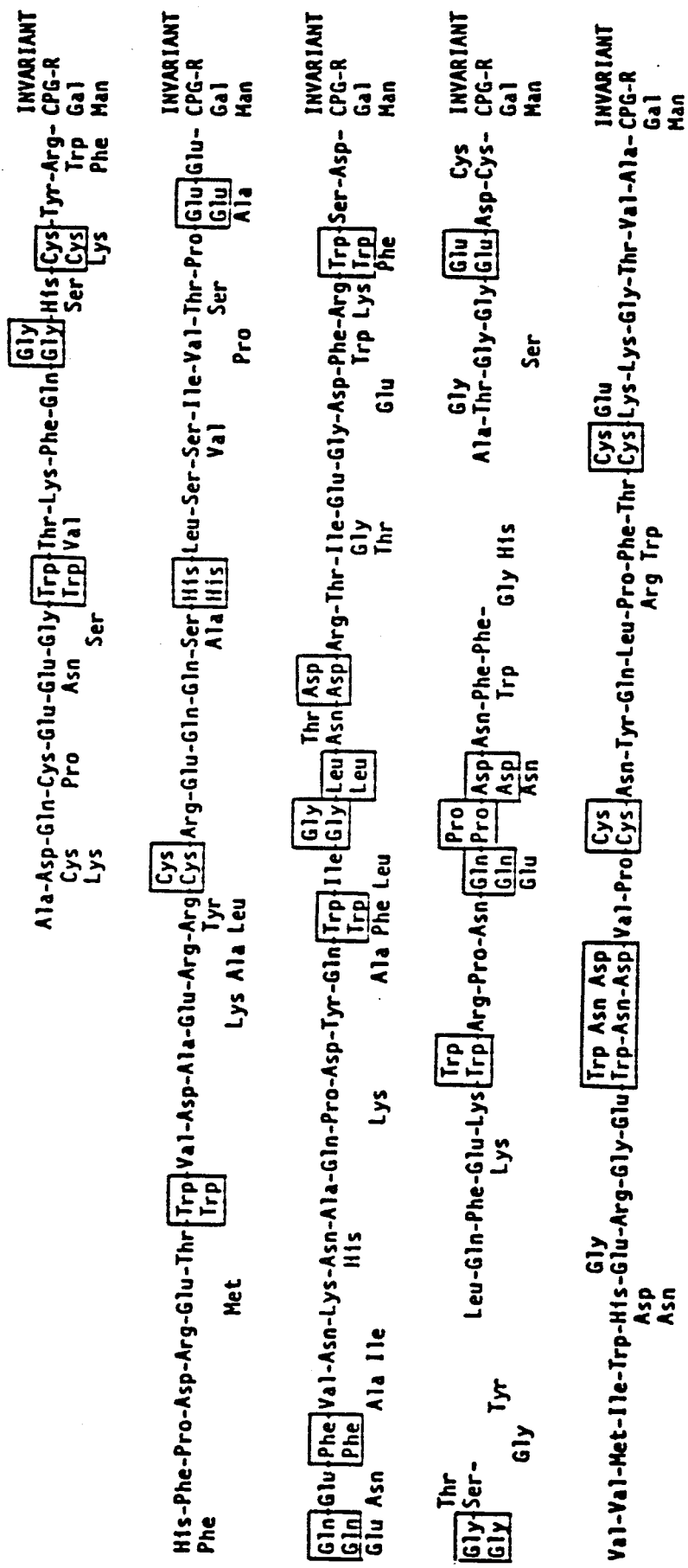

FIG. 5 is a comparison of the amino acid sequence of human mannose-binding protein with other lectins; invariant regions are shown on the top line, and galactose and mannose-specific regions on the lower lines. On the second line is shown the complete sequence of core proteoglycan receptor (CPG-R), a protein that binds galactose.

HUMAN MANNOSE-BINDING PROTEIN (MBP-HUMAN)

MBP-human is a soluble lectin like molecule which is synthesized in hepatocytes and released into the bloodstream. Generally, MBP-human is able to bind carbohydrates (such as mannose, N-acetylglucosamine, or fucose) at its carbohydrate binding domain and, therefore, is able to selectively recognize (or target) configurations of high mannose, N-acetylglucosamine, or fucose which are present on pathogens. Interaction of MBP-human with mannose rich pathogens enhances clearance of these pathogen by phagocytosis or results in activation of complement via the alternative complement pathway.

MBP-human can be isolated generally as described by Wild et al., supra, and Drickamer et al. supra, for example, by passage down a mannose-sepharose column.

Figure 1:
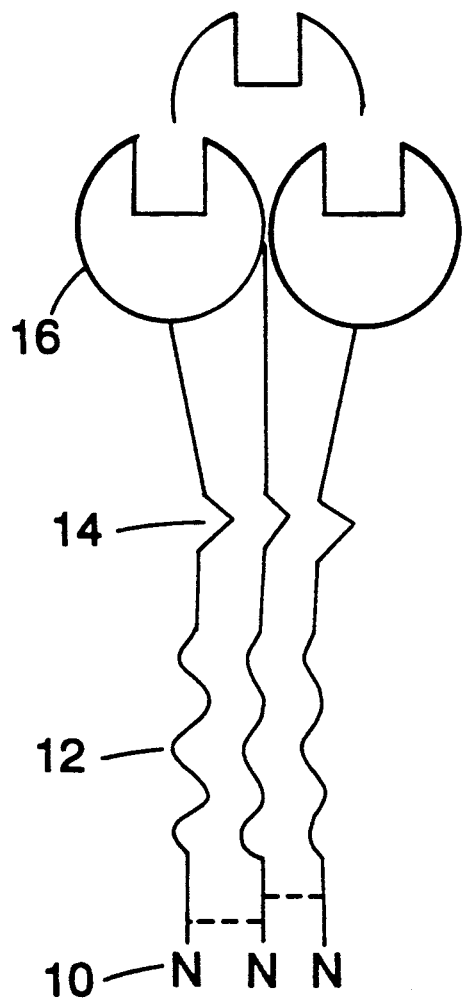
FIG. 1 is a diagram of a proposed model of human mannose-binding protein.

The general structure of MBP-human is shown in FIG. 1.; the cDNA sequence (with Exon boundaries indicated) and corresponding amino acid sequence are shown in FIGS. 2A and 2B. The amino terminal end 10 (corresponding to Exon 1. nucleotide bases 1-252).is cysteine rich, consistent with the formation of multimers in the native molecule by interchain disulfide bridges. Adjacent this region is a collagen-like segment 12 (Exon 2, nucleotide bases 253-369) having a repeated pattern of Gly X-Y (Gly represents glycine; X and Y are other amino acids), similar to those of non-fibrillar collagen genes. The structure of this segment is consistent with that of an effector region that interacts with complement components. Segment 14 (Exon 3, nucleotide bases 370-438) represents a putative cell attachment domain which facilitates attachment and ingestion by phagocyte cells. Segment 16 is a carboxy-terminal carbohydrate recognition domain (Exon 4, nucleotide bases 439-813). The mannose-binding domain is within this region.

Nucleic acid, for example, DNA, encoding MBP-human can be isolated by standard techniques. For example, oligonucleotide probes specific for the nucleic acid may be constructed and used to probe either genomic or cDNA libraries, as described by Drickamer et al., supra. Alternatively, gene fragments from related genes can be used as probes. Preferably, the probe is homologous (or closely related in sequence) to a region of the carbohydrate binding domain of MBP-human. The clones isolated by this technique contain engineered nucleic acid. Once isolated, the gene encoding MBP-human is useful for producing recombinant MBP-human protein, or peptide fragments thereof. In addition, the nucleic acid can be modified by standard techniques in order to express the same or modified peptides; e.g., by conservative base substitution the nucleic acid can be modified and still encode the same amino acid sequence, or the nucleic acid can be modified to encode a conservative amino acid substitution, which will preserve the tertiary structure and the distribution of charged amino acids in the peptide.

Examples of cloning MBP-human encoding nucleic acid are provided below. These examples are not limiting to the invention and one skilled in the art will recognize that there are many equivalent means for accomplishing similar results.

EXAMPLE 1 cDNA Clones

A human liver cDNA library was constructed in pKT218 by standard technique as described by Woods et al. *Proc. Natl. Acad. Sci. USA.* 79:5661, 1982. This library was probed using a gel purified radiolabelled rat MBP-C cDNA sequence digested with XhoI and EcoRI as described by Drickamer et al., supra. This probe was used under non-stringent conditions to identify potentially useful clones. The filters were prehybridized for 1 hour at 42° C. in 0.75M NaCl, 50 mM sodium phosphate, pH 7.4, 5 mM EDTA, 5x Denhardt's solution and 0.1% SDS (5x SSC), and then hybridized overnight at 42° C. The filters were washed at 45° C. in 2x SSC for 30 minutes and then in 1x SSC for 30 minutes. In addition, a HEPG2 λgt10 cDNA library plated in *E. coli* C600 was screened, as described by Kwiatkowski et al. *Nature* 323:455, 1986.

Figure 3:
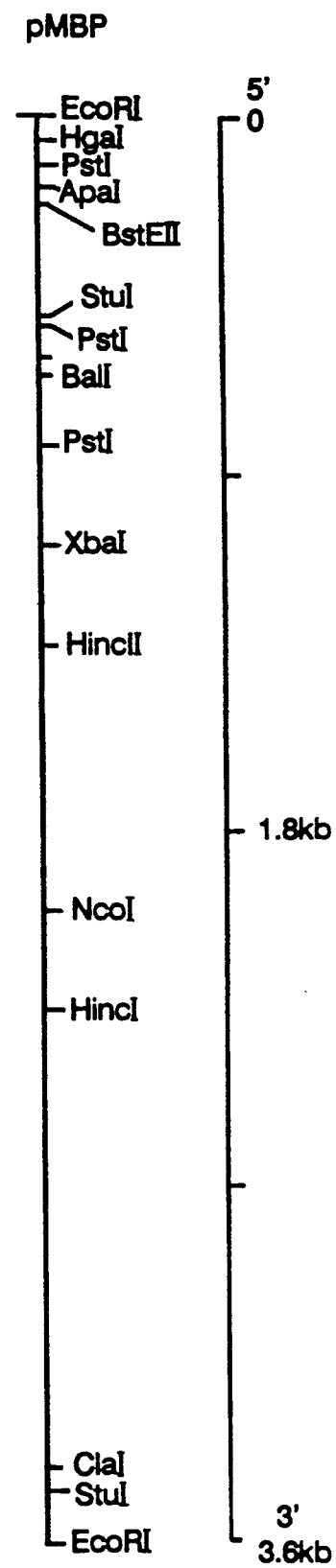
FIG. 3 is a restriction endonuclease map of the human mannose-binding protein cDNA insertin pMBP.

Five clones, including pMBP, were isolated and their sequences determined by the method of Sanger et al. (*Proc. Natl. Acad. Sci. USA* 74:5463, 1977) using M13, Mp18 cloning vectors (Messing et al. *Proc. Nat. Acad. Sci. U.S.A.* 74:3642, 1977). This sequence is provided in FIG. 2. The restriction map of pMBP is provided in FIG. 3; it has a 3.6 kb EcoRI insert isolated from the above λgt10 library.

EXAMPLE 2

Genomic Clone

The 650 bp carboxy terminal Pst-1 fragment (FIG. 3) of a MBP-human cDNA clone was used as a probe for a human genomic library. This library was constructed by standard techniques in EMBL 3A by inserting MboI-digested genomic DNA into the BamHI site. Clones which hybridized under stringent conditions were isolated. Specifically, the hybridization was performed as described above, except the wash conditions were at 68° C. in 0.1x SSC. The positively identified clones were plaque purified and their nucleic acid sequence (FIGS. 4A and 4B) determined as above.

Expression of MBP-human peptide fragments is by standard procedure. For example, the desired region of the MBP-human encoding DNA, preferably the cDNA, can be isolated from one of the above-described clones and inserted into any one of several standard expression vectors. A preferred region for expression is that encoding the carbohydrate binding domain, most preferably the mannose binding domain. In addition, the other regions of MBP-human can cooperate to target cells expressing mannose. The carbohydrate binding domain included in a 447bp fragment which includes nucleotide bases 366-813 (FIG. 2A). To identify the desired region more specifically, the sequence is compared to that in related proteins such as human mannose receptor.

In order to show that any particular region of MBP-human does bind mannose, the cDNA encoding it can be engineered by standard procedures to produce clones containing just this region. The resulting cloned DNA is then inserted into an expression vector. The peptide produced by such a vector is then passed through a mannose-sepharose column to see whether it will bind to mannose. Alternatively, a radioimmunoassay can be performed to see if radiolabelled mannose will react with the expressed peptide. Those peptides which bind mannose are among those useful in this invention.

It is unlikely that a single short linear region of amino acids of the MBP-human peptide is involved in binding to mannose, rather two or more such regions will probably cooperate to form a three-dimensional peptide configuration which can interact with, and bind, mannose. Such regions can be identified by comparison to other mannose-binding proteins as described above, and the DNA fragment encoding all such regions cloned and expressed. Such a DNA fragment is likely to be at least 60-90 base pairs in length, encoding at least 20-30 amino acids.

Referring to FIG. 5, such a comparison was performed by comparing other lectins, with mannose or other sugar binding specificities, to MBP-human. The sequences (except for the MBP sequence) and the alignment used in FIG. 5 were obtained from Drickamer et al., then in press, now (1987) *Kidney International* 32:67-94. The lower line of the figure shows a concensus for mannose binding proteins, the amino acids on this line and in the upper line (showing invariant amino acids) are the most important for binding to mannose. These results were obtained by comparison of MBP-human to lectin proteins including the human and rat hepatic asialoglycoprotein receptors (Drickamer, *J. Biol. Chem.* 263:9557, 1988), the avian heptic receptor (Drickamer, 1988 supra), the apoprotein of dog (Benson et al., *Proc. Natl. Acad. Sci. USA.* 82:6379, 1985) and human surfactant (White et al., *Nature* 317:361, 1985); the NH$_2$ portion of a galactose specific lectin isolated from the hemolymph of *S. periginia* (Takahashi et al., *J. Biol. Chem.* 260:12228, 1985); a lectin isolated from the coelomic fluid of a sea urchin *A. crassispina* (Giga et al., *J. Biol. Chem.* 13:6197, 1987); a chicken cartilage core proteoglycan protein (Shigaku et al., *Proc. Natl. Acad. Sci USA.* 83:5081, 1986) and the IgE Fc receptor (Ikuta et al., *Proc. Natl. Acad. Sci. USA.* 84:819, 1987).

The above described mannose binding peptide, or the entire recombinant protein, is useful for specifically targeting (or specifically recognizing) cells expressing carbohydrates such as mannose, N-acetylglucosamine, or fucose on their surface, e.g., bacteria, fungi, and viruses. By linking this peptide to molecules able to kill or inhibit growth of such cells, a hybrid peptide of great therapeutic use can be constructed. For example, the toxic part of ricin and cholera toxin (i.e., the portion of the toxin molecule specifically able to kill or inhibit growth of cells), or chemicals such as AZT can be linked to this peptide. The nucleic acid encoding such toxins can be ligated to the mannose binding peptide-encoding nucleic acid and expressed as a single entity to form a hybrid peptide, for example, as described by Murphy U.S. Pat. No. 4,675,382, hereby incorporated by reference. (By ligated is meant linked enzymatically or chemically to form a single nucleic acid entity.) Alternatively, the two peptides can be synthesized separately and linked chemically, for example, as described by Ross U.S. Pat. No. 4,275,000, hereby incorporated by reference.

Another region for expression includes the complement fixing domain at nucleotide bases 253-369 (FIG. 2A). The specific segment of nucleic acid which encodes a useful complement fixing portion of MBP-human can be identified by standard technique, using methods similar to those described above for identifying portions able to bind mannose. The peptide produced by an expression vector containing DNA cloned from such a region can be isolated by ion-exchange chromatography and linked to a molecule capable of binding as a cognate molecule, to a specific virus. Such a chimeric peptide is able to bind to the specific virus, and mediate complement fixation and thus the inactivation of the virus. By cognate molecule is meant a molecule that binds its target molecule as a lock and key.

Expression vectors suitable for peptide expression include standard bacterial (e.g., pKK233-2, Amann et al. *Gene* in press, sold by Pharmacia, 800 Centennial Avenue, Piscataway, N.J. 08854), yeast, and viral expression vectors, as well as eucaryotic vectors. Those skilled in the art will realise that such vectors generally are suitable for expressing the protein, and the example below is not limiting to this invention.

EXAMPLE 3

Expression of Peptides

A human mannose-binding protein cDNA clone representing the coding region from the first in-frame ATG to the termination codon (nucleotide bases 66-813, FIGS. 2A and 2B) was prepared and XhoI linkers ligated at both ends of the cDNA. The cDNA was subcloned into a newly constructed vector containing the pBR322 origin of replication, immunoglobin heavy chain enhancer, metallothionein promoter, XhoI cloning site, a polyadenylation signal and a dihydrofolate reductase gene. The vector was digested with XhoI, and the cDNA was ligated into the vector. This DNA was then transfected into NS-1 myeloma cells by standard procedure (*Cloning, A Laboratory Manual*, ed, Pouwels et al., Elsevier Science Pub., 52 Vanderbilt Avenue, NY, N.Y. 10017, 1985) in the presence of methotrexate and colonies resistant to methotrexate selected. A clone which secreted 20 to 40 μg/ml of recombinant mannose-binding protein was identified and expanded and recombinant mannose binding protein recovered on a mannan-sepharose column.

In a second construction, a fragment beginning at nucleotide 366 and extending to nucleotide 813 (FIGS. 2A and 2B) containing the carbohydrate recognition domain, 80 MBP-human, was constructed and ligated at the 5' end to the immunoglobulin heavy chain signal peptide sequence containing an in-frame initiator codon. XhoI linkers were ligated at both ends of the fragment, the cDNA was subcloned into a XhoI vector, the DNA was transfected into NS-1 myoloma cells, colonies resistant to methotrexate were selected, and the recombinant polypeptide was recovered as described above. This polypeptide contains the carbohydrate recognition domain alone of mannose binding proteins and is able to recognize bacterial targets which are rich in mannose, N-acetylglucosamine, and fucose.

Expression of human mannose-binding peptides by these vectors and organisms can be followed using a sepharose-mannose column. The column is first contacted with the expressed material. Peptides able to recognize and bind mannose are bound to the mannose-sepharose matrix, eluted with 50 mM Tris/10 mM EDTA, and identified using 8% polyacrylamide gels (with Laemmli buffers, *Nature* 227:600, 1970). Those clones which produce mannose binding peptides, i.e., peptides which bind to such a column, are among those useful in this invention.

Antibodies to expressed peptides such as those described above can be produced by standard techniques. Peptides useful for preparation of such antibodies are identified by standard procedure, e.g., by determining those that induce antibodies which immunologically react with MBP-human. The antibodies may be monoclonal or polyclonal and are useful for identification of the peptides within animal serum or in clinical diagnostic tests.

Use

Exposed mannose is a feature of the cell walls of many pathogens, whereas higher organisms, including humans and animals, tend to have processed membrane glycoproteins having complex sugars which mask internal mannose residues. These internal mannose residues are not recognized by MBPs. Native or recombinant mannose binding proteins, or chimeric peptides containing the mannose binding domain, are useful therapeutic agents. These proteins or peptides specifically bind mannose-rich pathogens, including bacteria, fungi, yeasts, parasites, or the envelope glycoproteins of certain viruses, and thus direct removal of such pathogens from the animal.

For non-viral pathogens, efficacy of removal by host defense mechanisms may be increased by directing attachment of the mannose binding protein complex to the surface of phagocyte cells, thereby enhancing the clearance of the pathogens from the circulation, by causing the phagocytes to recognize these pathogens.

For viruses, which express mannose-rich glycoproteins, direct inactivation of the virus and viral infected cells is enhanced by attaching toxins, such as ricin, cholera, or diptheria or antimetabolite drugs, such as AZT, to a therapeutic peptide containing the mannose binding domain of the mannose-binding protein, as described earlier. For example, the fragment from base pair 366 to 813 shown in FIGS. 2A and 2B containing the carboxy-terminal mannose binding domain of MBP-human can be expressed in an expression vector (see example 3 above) and the peptide produced linked chemically, at the amino terminal end, to a toxic nucleotide analog such as dideoxycytosine or AZT. The hybrid peptide thus formed can serve to kill or inhibit growth of the target cell.

The amino terminal portion of human mannose-binding protein including the complement binding domain, encoded by the nucleic acid from nucleotide-bases at position 66–366 of FIG. 2A can be covalently binded (at its carboxy-terminal end) to the first 180 amino acids of the CD4 receptor protein of T lymphocytes. This domain of CD4 is able to bind to the envelope glycoprotein of the Human Immunodeficiency Virus or HIV (the virus thought to cause Acquired Immunodeficiency Syndrome or AIDS) as described by Berger et al., *Proc. Natl. Acad. Sci., USA* 85:2357-2361, 1988. Consequently, this construction of the mannose-binding protein-CD4 fusion protein can be aimed at targeting HIV via the CD4 domain, and mediating complement fixation via the mannose-binding protein fragment.

Alternatively, a peptide such as that prepared in example 3, which contains the mannose-binding region of MBP-human without the complement binding domain, can be used to target HIV. As shown below, fluorescently-labelled such peptides do not bind to cells uninfected with HIV but do bind to infected cells. The resulting product should be particularly effective in specifically targeting drug-like molecules to HIV or HIV-infected cells without a concurrent activation of complement.

EXAMPLE 4

HIV Targeting

MBP-human was shown to be effective in vitro for preventing infection of H9 CD4+ cells with HIV. Purified HIV was incubated in the presence or absence of highly purified homogenous MBP-human (prepared as described by Summerfield et al., *Bioc. et Biop. Acta* 883:197, 1986; Wild et al., *Biochem. J.* 210:167, 1983; Townsend et al., *Biochem. J.* 194:209, 1981; and Kawasaki et al., *J. Biochem.* 94:937, 1983). The treated virus was then incubated with H9 CD4+ lymphocytes (which are primary targets for HIV infection), and 7 days later viral infectivity was measured by a) the appearance of HIV envelope glycoprotein (which was assayed on the cell surface by immunofluorescence using specific anti-envelope glycoprotein antisera) and b) the presence of reverse transcriptase activity (which is present only when the cell is infected with HIV). MBP-human completely inhibits viral entry into cells. This was shown by the absence of HIV envelope glycoprotein on the cell surface, and by undetectable reverse transcriptase activity. Control experiments showed that the inhibition by MBP-human was specific; these experiments involved competing MBP human with mannose rich yeast mannan, and neo-glycoprotein mannose BSA.

In experiments using fluorescently-labelled MBP-human to observe binding to infected or uninfected cells, the fluorescently-labelled MBP-human was used to show that mannan and mannose-BSA inhibits the binding of MBP-human to virally infected cells, and that MBP-human does not bind uninfected H9 cells. Thus MBP-human is recognizing exposed mannose units on these cells.

Thus, MBP-human or the mannose binding domain thereof are suitable for identifying cells infected with HIV, or related viruses which express mannose rich envelope glycoproteins on their cell surface. MBP-human, the mannose binding domain, or chimeric or altered molecules thereof can be used to target cytotoxic agents to directly and specifically kill infected cells. Further, these molecules can be used to prevent the spread of viral infection, and even the initial infection itself.

MBP-human and related peptides as described above may be administered by routine methods in pharmaceutically acceptable carrier substances, i.e., inert substances suitable for pharmaceutical use such as the dispensing of drugs or medicine. For example, they can be injected directly into the blood stream of an animal, especially humans, to a level of between 1–500 µg/ml serum (most preferably, 150 µg/ml) final concentration, and this dose repeated to maintain this level. They can be administered prophylactically or after infection to treat, for example, pneumocystis. In another prophylactic use, MBP-human may be used to coat intravenous or urethral catheters (e.g., by chemical impregnation of the catheter material with MBP-human or related peptides) to prevent infection in immunocompromised patients (e.g., cancer patients subjected to long term intravenous chemotherapy). Such catheters will bind infective organisms and prevent their entry into the patient. The peptides may be administered orally, injected subcutaneously, or applied in powder or lotion form (at a concentration of between 5–100 µg/ml, preferably 25 µg/ml), for example, to treat local infections, such as bacterial infection, yeast infection, or infection with *Trichophyton*, which causes athlete's foot.

Another use of these peptides is in the determination of an animal's susceptibility to infection by agents such as HIV. Here, the serum level of MBPs in the animal is measured using antibodies raised against MBP-human, or related peptides, in for example, an ELISA protocol. The level of MBPs in the serum can then be related to the susceptibility to infection of this animal to an agent, and this relationship used to estimate other animals' susceptibility. Thus, for example if a high level of MBP human is linked to low susceptibility to infection by HIV, then a human having a low level of MBP-human is likely to be susceptible to HIV infection. Further, at the genomic level, such susceptibility may be related to defects in the nucleic acid. Such defects can be discovered using the cloned MBP-human genes, or fragments thereof, as probes. Polymorphisms linked to HIV susceptibility can be detected and used to predict susceptibility of other humans to infection.

MBPs can also be used as a diagnostic tool, e.g., for the diagnosis of fungal diseases. Fungi infecting an animal will shed a mannose-rich polysaccharide into the serum. One hundred µl of serum from a patient can be analyzed with fluorescently-labelled MBP-human to observe binding to the fungal polysaccharide coat, and the degree of binding can be related to the degree of fungal infection remaining following a course of treatment. Appropriate subseguent treatment can be planned accordingly.

The presence of MBP human can be used as an indicator of imminent infection, especially in newborns. The acute phase response is a nonspecific primitive response to stress, inducing the synthesis of a variety of proteins which are secreted in the liver. Synthesis of mannose-binding protein is part of this response to stress and infection (Ezekowitz et al. *J. Exp. Med.* 167:1034, 1988), and therefore the presence of increased levels of MBP-human can be a predictor of imminent infection. Analysis of blood from 12 premature infants shows that high levels of mannose-binding protein (i.e., greater than 50 μg/ml serum) correlates with infection. In three infants, raised mannose binding protein levels preceded the clinical signs of infection. Detection of high levels of mannose binding protein can provide a useful and sensitive assay for predicting imminent infection in infants, thereby allowing administration of the appropriate treatment before the infection becomes established.

Deposits

Plasmid pMBP, in *E. coli*, was deposited on Aug. 4, 1987, with the American Type Culture Collection (ATCC) where the deposit was given the accession number ATCC 67483.

Applicant's assignee, Children's Medical Center Corporation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Other embodiments are within the following claims.

I claim:

1. An isolated nucleic acid encoding human mannose-binding protein, said human mannose-binding protein having the sequence encoded by plasmid pMBP deposited in the ATCC as strain number ATCC 67483.

2. An isolated nucleic acid comprising a nucleic acid sequence encoding a polypeptide, said polypeptide comprising at least 20 contiguous amino acids of the carbohydrate binding domain of the human mannose-binding protein encoded by plasmid pMBP deposited in the ATCC as strain number ATCC 67483, said polypeptide being characterized by the ability to bind specifically to cells expressing mannose, N-acetylglucosamine, or fucose.

3. The isolated nucleic acid of claim 2 wherein said polypeptide comprises the Exon 4 sequence shown in FIGS. 2A and 2B.

4. An isolated nucleic acid comprising a nucleic acid sequence encoding a polypeptide, said polypeptide comprising at least 20 contiguous amino acids of the complement fixing domain of the human mannose-binding protein encoded by plasmid pMBP deposited in the ATCC as strain number ATCC 67483, said polypeptide being characterized by the ability to fix complement.

5. The isolated nucleic acid of claim 4 wherein said polypeptide comprises the Exon 2 sequence shown in FIGS. 2A and 2B.

6. The isolated nucleic acid of any of claim 1 and 2-5 wherein said nucleic acid is cDNA.

7. The isolated nucleic acid of claim 2 or claim 4 wherein said nucleic acid is ligated to nucleic acid encoding at least a toxic portion of a cytotoxin.

8. The isolated nucleic acid of claim 7 wherein said cytotoxin is chosen from dideoxycytosine, AZT, ricin, diphtheria toxin, or cholera toxin.

9. The isolated nucleic acid of claims 4 or 5 wherein said nucleic acid is ligated to nucleic acid encoding a portion of the CD4 molecule characterized by its ability to bind to a Human Immunodeficiency virus (HIV).

10. An expression vector comprising the isolated nucleic acid of any one of claims 1, 2 and 4.

11. A recombinant cell comprising the isolated nucleic acid of any one of claims 1, 2 and 4.

12. The cell of claim 11 wherein said cell is a bacterium, fungus, or eucaryotic cell.

13. The cell of claim 12 wherein said cell is:
a) an *Escherichia coli* cell;
b) a yeast cell; or
c) a cultured eucaryotic cell line.

* * * * *